United States Patent [19]
Thomas et al.

[11] Patent Number: 5,968,062
[45] Date of Patent: *Oct. 19, 1999

[54] SURGICAL CUTTING DEVICE REMOVEABLY CONNECTED TO A ROTARTY DRIVE ELEMENT

[75] Inventors: James Cooper Thomas, Las Vegas, Nev.; Rick D. Roberts, Moorpark, Calif.

[73] Assignee: Surgical Dynamics, Inc., Norwalk, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/914,016

[22] Filed: Aug. 4, 1997

Related U.S. Application Data

[63] Continuation of application No. 08/695,984, Aug. 15, 1996, abandoned
[60] Provisional application No. 60/015,390, Apr. 12, 1996.

[51] Int. Cl.[6] .................................................. A61B 17/14
[52] U.S. Cl. .......................................... 606/180; 606/160
[58] Field of Search ................................... 606/180, 170, 606/167, 79, 80, 159, 160, 166

[56] References Cited

U.S. PATENT DOCUMENTS

| | | |
|---|---|---|
| 68,647 | 9/1867 | Palmer . |
| 737,293 | 8/1903 | Summerfeldt . |
| 752,356 | 2/1904 | Filling . |
| 1,625,906 | 4/1927 | Naylor . |
| 1,663,761 | 3/1928 | Johnson . |
| 1,837,503 | 12/1931 | Thostenson . |
| 2,082,982 | 6/1937 | Schumacher . |
| 2,505,917 | 5/1950 | Schumacher . |
| 2,601,513 | 6/1952 | Gladstone . |
| 2,676,595 | 4/1954 | Dyekjaer ................................. 128/305 |
| 2,730,101 | 1/1956 | Hoffman ................................. 128/305 |
| 2,816,552 | 12/1957 | Hoffman ................................. 128/305 |
| 2,876,777 | 3/1959 | Kees, Jr. . |
| 3,336,927 | 8/1967 | Klebanoff ............................... 128/305 |
| 3,502,082 | 3/1970 | Chatfield . |
| 3,635,222 | 1/1972 | Robinson . |
| 3,670,732 | 6/1972 | Robinson ............................... 128/297 |
| 3,688,407 | 9/1972 | Paquette . |
| 3,996,935 | 12/1976 | Banko .................................... 606/166 |
| 4,020,847 | 5/1977 | Clark. III ............................... 128/305 |
| 4,043,322 | 8/1977 | Robinson . |
| 4,167,943 | 9/1979 | Banko .................................... 128/305 |
| 4,274,414 | 6/1981 | Johnson et al. ......................... 128/305 |
| 4,311,140 | 1/1982 | Bridgman . |
| 4,603,694 | 8/1986 | Wheeler ................................. 128/312 |
| 4,728,319 | 3/1988 | Masch . |
| 4,763,414 | 8/1988 | McNeill, II . |

(List continued on next page.)

FOREIGN PATENT DOCUMENTS

| | | |
|---|---|---|
| 36537 | 9/1926 | Germany . |
| 1150232 | 4/1969 | United Kingdom . |
| WO 90/02524 | 3/1990 | WIPO . |

OTHER PUBLICATIONS

Surgical Dynamics, Nucleotome System Automated Percutaneous Lumbar Discectomy, 1990, 4 pp.

*Primary Examiner*—Michael Powell Buiz
*Assistant Examiner*—Kevin Truong

[57] ABSTRACT

A cutting device for the cutting and reduction of matter from a surgical site having a cutting head having an entry tip and a cutting blade positioned on opposed leading edges of a window formed through the interior of the cutting head. The window includes angled walls extending from each cutting blade along the circumference of the window. The cutting head is attached to a shaft for mounting the cutting device to a rotary surgical drill. The matter is removed and further reduced as the cutting head is rotated at the surgical site. The main shaft also includes depth markings for identifying the depth of the device in the surgical site. The geometry of the cutting head and entry tip can be varied for particular surgical procedures.

32 Claims, 5 Drawing Sheets

U.S. PATENT DOCUMENTS

| | | | |
|---|---|---|---|
| 4,819,635 | 4/1989 | Shapiro | 128/305 |
| 4,850,354 | 7/1989 | McGurk-Burleson et al. | 128/305 |
| 4,857,045 | 8/1989 | Rydell | 604/22 |
| 4,867,157 | 9/1989 | McGurk-Burleson et al. | 128/305 |
| 4,887,613 | 12/1989 | Farr et al. . | |
| 4,923,441 | 5/1990 | Shuler | 604/22 |
| 4,983,179 | 1/1991 | Sjostrom | 606/180 |
| 4,986,807 | 1/1991 | Farr | 604/22 |
| 5,007,917 | 4/1991 | Evans | 606/170 |
| 5,019,088 | 5/1991 | Farr | 606/159 |
| 5,112,345 | 5/1992 | Farr . | |
| 5,116,346 | 5/1992 | Yeh | 606/131 |
| 5,122,134 | 6/1992 | Borzone et al. . | |
| 5,160,318 | 11/1992 | Shuler | 604/22 |
| 5,176,628 | 1/1993 | Charles et al. | 604/22 |
| 5,176,693 | 1/1993 | Pannek, Jr. . | |
| 5,192,291 | 3/1993 | Pannek, Jr. . | |
| 5,222,959 | 6/1993 | Anis | 606/107 |
| 5,222,965 | 6/1993 | Haughton | 606/159 |
| 5,224,945 | 7/1993 | Pannek, Jr. . | |
| 5,250,061 | 10/1993 | Michelson . | |
| 5,269,787 | 12/1993 | Cozean, Jr. et al. . | |
| 5,275,609 | 1/1994 | Pingleton et al. | 606/170 |
| 5,282,816 | 2/1994 | Miller et al. . | |
| 5,324,301 | 6/1994 | Drucker | 606/180 |
| 5,366,468 | 11/1994 | Fucci et al. . | |
| 5,376,100 | 12/1994 | Lefebvre . | |
| 5,383,884 | 1/1995 | Summers | 606/170 |
| 5,403,276 | 4/1995 | Schechter et al. | 604/22 |
| 5,437,675 | 8/1995 | Wilson | 606/180 |
| 5,456,689 | 10/1995 | Kresch et al. . | |
| 5,474,532 | 12/1995 | Steppe . | |
| 5,489,291 | 2/1996 | Wiley | 606/170 |
| 5,492,528 | 2/1996 | Anis | 604/22 |
| 5,509,923 | 4/1996 | Middleman et al. . | |
| 5,556,408 | 9/1996 | Farhat . | |
| 5,571,122 | 11/1996 | Kelly et al. . | |
| 5,571,131 | 11/1996 | Ek et al. | 606/170 |
| 5,613,972 | 3/1997 | Lee et al. . | |
| 5,632,756 | 5/1997 | Kruglick . | |
| 5,722,985 | 3/1998 | Pettus | 606/180 |

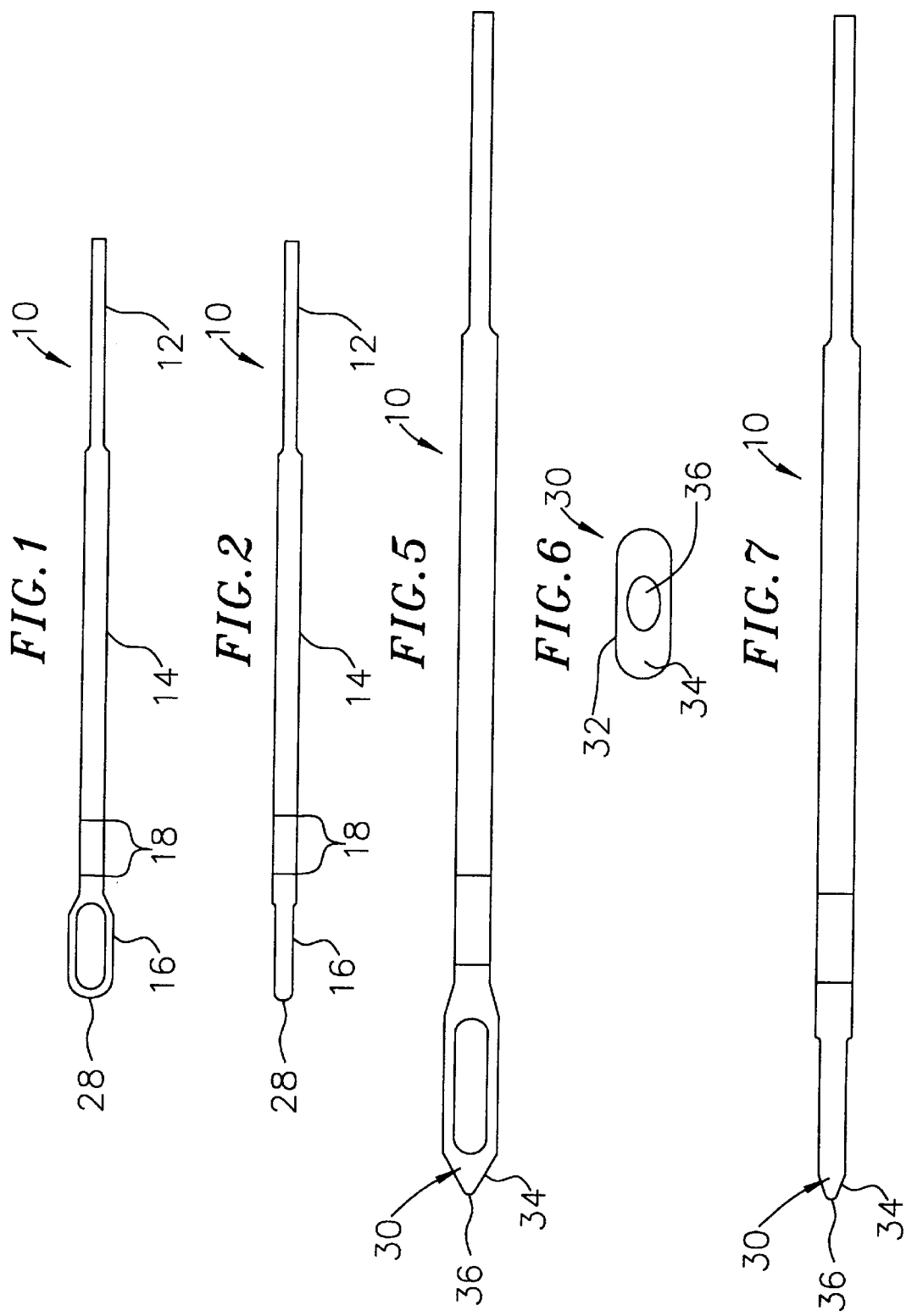

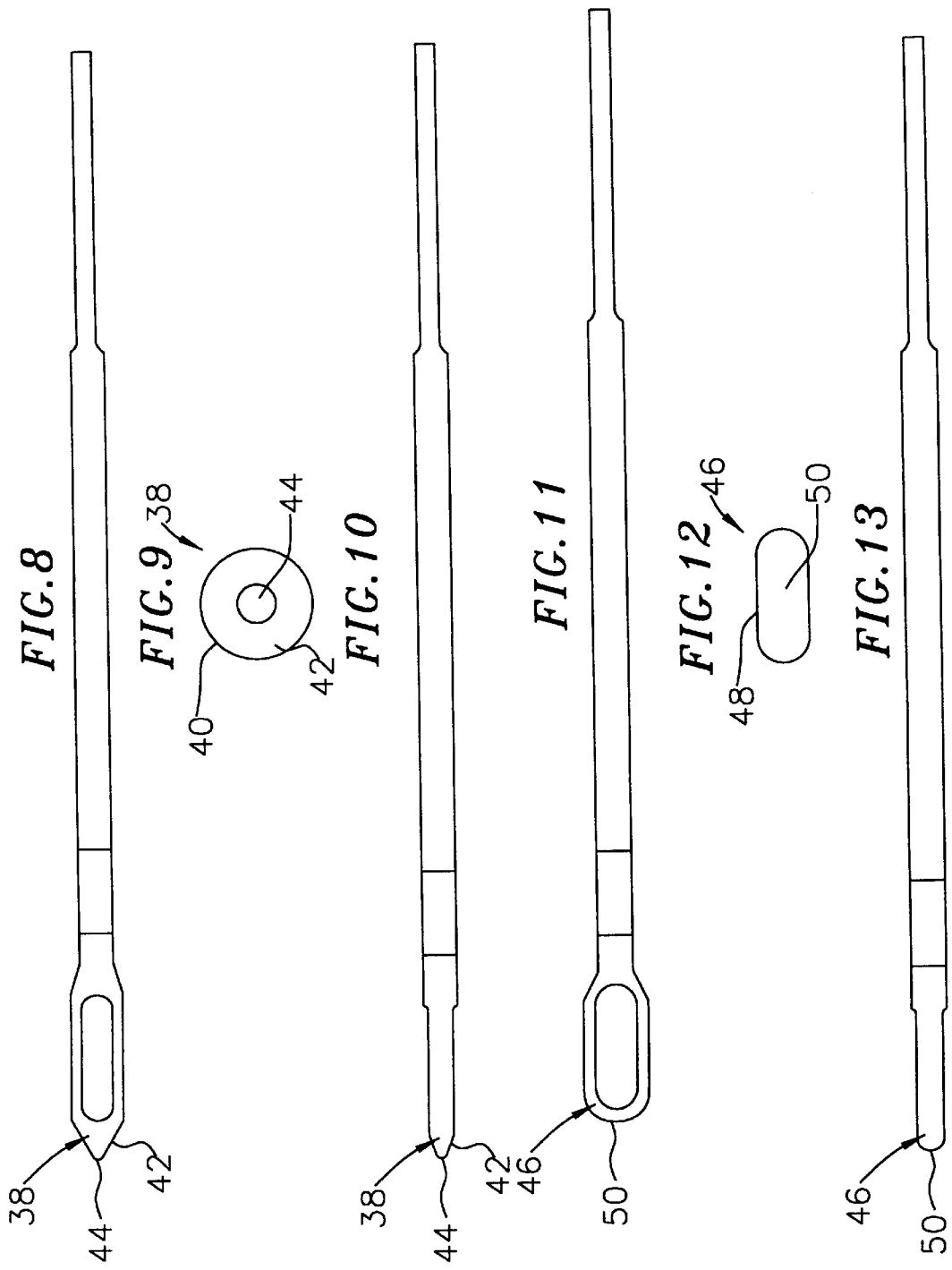

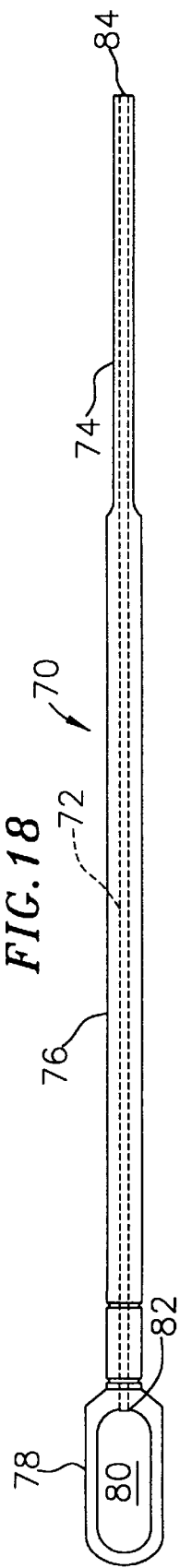
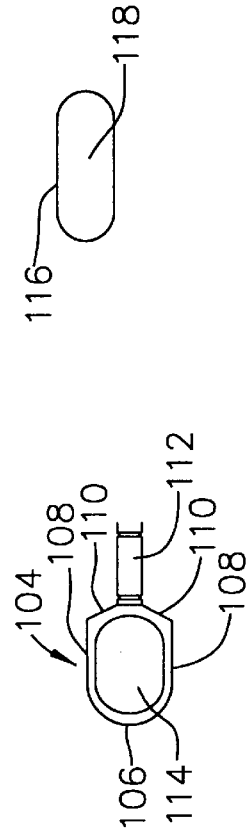
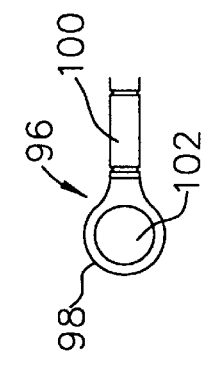
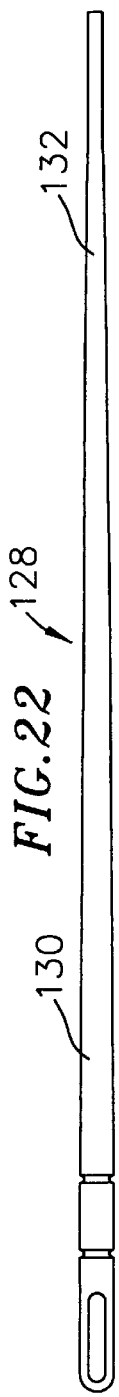

SURGICAL CUTTING DEVICE REMOVEABLY CONNECTED TO A ROTARTY DRIVE ELEMENT

CROSS-REFERENCE TO RELATED APPLICATION

This is a continuation of application Ser. No. 08/695,984, filed Aug. 15, 1996 now abandoned. This application is based on and claims priority of provisional application Ser. No. 60/015,390, filed Apr. 12, 1996.

BACKGROUND OF THE INVENTION

This invention relates generally to devices used in surgical procedures, such as, for example, endoscopic diskectomy and endoscopic spinal fusion. More specifically, the invention relates to a rotatable surgical cutting device which is removably connected to a rotary drive element.

FIELD OF THE INVENTION

In the United States, spinal disk problems are the most common cause of disability of people under 45 years of age. There are currently 5.2 million Americans either temporarily or permanently disabled as a result of chronic back pain. Approximately 220,000 spinal operations are performed in America each year to combat the disabilities caused by spinal disk problems.

A common problem among patients suffering from chronic back pain is a protruding lumbar intervertebral disc. This condition occurs when a portion of the disk protrudes into the spinal canal space and creates pressure on a nerve. A patient may also experience a partial or complete collapse of an intervertebral disk, resulting in spinal instability, immobility and severe chronic pain.

It is often necessary to surgically remove offending disk material from the spinal canal to improve the spinal function of the patient and to relieve chronic pain. In some cases it is also necessary to perform a spinal fusion, to improve spinal stability and to provide additional support for any damaged intervertebral disk.

Procedures such as endoscopic diskectomy can be used for the removal of fibrous intervertebral tissue. Endoscopic surgeries are accomplished by creating small openings or "ports" in the body, through which various small instruments or a camera may be inserted and manipulated to observe or work in the disk space area. Current endoscopic procedures utilized for the removal of disk material rely primarily upon automated or manual methods. (Surgical Dynamics Nucleotome or the Soframor-Danek Diskector). These methods remove intervertebral disk material by using a guillotine cutting blade, with the aspiration of disk material into a port connected to a cannula, once the device is activated.

For open spinal fusions, products currently available for the removal of intervertebral disk tissue include the Acromed manual PLIG instrumentation and the Cloward PLIF set instrumentation. These instruments are manual in operation and utilize rasps and rongeurs, whereby disk material is removed by increasing the size of the rasp sequentially.

Based upon the current instrumentation and procedures available for the removal of intervertebral disk material and the preparation of bone graft sites, there remains an opportunity to improve the speed, accuracy and effectiveness of these procedures. In addition, animal studies have indicated that circular holes in the intervertebral disk space provide an improved response to healing over those that are square, rectangular, or cruciate in shape. Therefore, an opportunity exists for the introduction of a device that will provide a smooth circular void in the intervertebral disk space, allowing for improved healing of the annular opening.

Also due to the tenacious adhesion of the disk material to the vertebral end plate, an opportunity exists for a more efficient and effective method of removing disk material from this area of the vertebra in preparation for bone grafts.

Lastly, there remains an opportunity to reduce the amount of trauma suffered by the patient during back surgery, as the result of instrument movement and manipulation in and around the spinal canal and surrounding pathology.

SUMMARY OF THE INVENTION

The invention is a surgical cutting device constructed from one piece of hardened surgical steel. The device has a proximal end comprising a mounting shaft, a main shaft, and depth indicators located on the main shaft. The device also includes a cutting head positioned at the end of the main shaft at the distal end of the device.

The mounting shaft is designed to fit into any standard low or high speed rotary surgical drill. The cutting device is attached to and removable from the rotary drill in the same manner as currently available rotary tools and accessories, namely by placing the mounting shaft into the friction lock collet of the drill. The main shaft of the cutting device is designed in various lengths to enable the use of the device for both cannulated endoscopic surgeries, or non-cannulated open back surgeries. The depth indicators provide a method for the instantaneous observation of cutting depth when the device is in the intervertebral disk space. These indicators also serve to alert the surgeon to over-penetration into the disk wall.

The cutting head of the device includes two cutting blades and an entry tip. The two-bladed configuration of the cutting head forms a window between the cutting blades providing an area for removed disk material to accumulate and be further reduced in density.

The cutting head of the device is designed with various outside diameters and tip configurations. The various head diameters allow for the device to be used for the removal of disk material in the cervical, thoracic or lumbar regions of the spine, based upon the pathology and intervertebral disk space of the patient. The unique design of the head enables the smooth and accurate entry of the device into the intervertebral disk space, while simultaneously cutting and reducing the density of the removed intervertebral fibro cartilaginous disc material. The head of the device is also designed to perform decortication of bone if desired, either simultaneously or independently to the removal of the disk material. Based upon the requirements of the surgical procedure, the surgeon may select one or more of the various tip configurations to perform the disk removal procedure. Also, by using a series of incrementally increasing diameter heads, the surgeon can accurately increase the size of the void created in the intervertebral disk space. This provides an evacuated disk space in preparation for a bone graft.

The primary head configurations of the device can be round, teardrop, bulb, or elliptical shaped and include a flat ended arrow style tip, a conical bullet style tip, an elliptical, circular, or rounded tip. The bullet and arrow style tips are designed to be used primarily for the initial entry into the intervertebral disk space. These tips provide a smooth entry into the annulus of the disk, to begin the intervertebral disk tissue removal process. The rounded tip is designed primarily to be used in a secondary operation, to increase the amount of disk material removed and to provide a smooth circular void in the disk. The round tip may also be used for the decortication of bone if desired. Based upon the procedure to be performed, the location of the injury and the position of the offending disk tissue, the surgeon will select the device head configuration, entry tip style and diameter accordingly.

The device may be used in a cannulated or non-cannulated fashion, based upon the surgical procedure to be performed. For an endoscopic surgical procedure, the device is used in a cannulated fashion using a standard surgical cannula and is designed to fit in most surgical cannulas currently available.

In the case of endoscopic surgeries, the device is placed through the skin and docked on the edge of the intervertebral disc. Once docked, the surgeon uses the surgical drill to rotate the head of the device to smoothly enter the annulus of the disc. As the device enters into the disk space, the disk tissue is cut and migrates to the elliptical opening at the center of the cutting head. As the procedure continues, the removed disk material is then further reduced in density, as a result of the spinning of the cutting blades.

The surgeon may then use the device to decorticate the vertebral end plate in preparation for a bone graft, using the same, or a different device diameter or tip configuration. Due to the reduction in density of the removed disk material, normal surgical irrigation and suction can be used to thoroughly flush the surgical site. Since the density of the disk material is reduced to an emulsion, rather than being trimmed or cut into fragments, the possibility of disk debris being left at the operation site is significantly reduced.

When used in open back surgery, the device is used in a non-cannulated fashion, utilizing a guard. In the case of these surgeries, the device is used to remove disk tissue and decorticate bone externally from the cannula, in the same manner as described above for endoscopic procedures.

In addition to spinal related surgeries, the surgical cutting device of the present invention is also applicable to other surgical procedures. For example, in hip surgery, the device can be used for the removal of soft tissue and the decortication of bone. In hip joint revision surgery, the device can be used for the removal of soft tissue, the decortication of bone and the removal of bone cement. In shoulder and shoulder joint replacement surgery, the device is also applicable for the removal of soft tissue and the decortication of bone. In knee surgery and knee joint replacement surgery, the device can also be used for the removal of soft tissue and the decortication of bone. In all types of surgeries, the device will be attached to a rotary drill and operate similarly to that in spinal surgery.

Additional procedures for which the device may be used include, but are not limited to, the micro lumbar laminectomy, the anterior or posterior inter-body lumbar diskectomy and fusion, the cervical anterior diskectomy and fusion and the anterior thoracic diskectomy and fusion.

Accordingly, some objectives of this invention are to provide a surgical cutting device capable of providing a circular hole in the intervertebral disk space for efficient disk removal during diskectomies and in preparation for bone grafting; provide a surgical device with the ability to accurately remove and reduce the density of intervertebral fibro cartilaginous disk material, and therefore reduce the possibility of disk debris being left in the intervertebral space. This removal of disk material improves bone graft contact and will improve fusion potential; and to minimize the degree of tissue trauma, by reducing the elapsed time and tool manipulation currently required to remove disk material and to prepare a site for bone grafting.

Additional advantages of the present invention will also become apparent from the accompanying detailed description and drawings.

BRIEF DESCRIPTION OF THE DRAWINGS

FIG. 1 is a top view of a typical cutting device;

FIG. 2 is a side view of the cutting device of FIG. 1;

FIG. 5 is a top view of a cutting device having an arrow style entry tip configuration;

FIG. 6 is an end view of the cutting device of FIG. 5.

FIG. 7 is a side view of the cutting device of FIG. 5;

FIG. 8 is a top view of cutting device having a bullet style entry tip configuration;

FIG. 9 is an end view of the cutting device of FIG. 8;

FIG. 10 is a side view of the cutting device of FIG. 8;

FIG. 11 is a top view of cutting device having a elliptical style entry tip configuration;

FIG. 12 is an end view of the cutting device of FIG. 11;

FIG. 13 is a side view of the cutting device of FIG. 11;

FIG. 18 is a side view of a self-aspirating embodiment of the cutting device of FIG. 1;

FIG. 19a is a top view of a round cutting head configuration of the cutting device;

FIG. 19b is a top view of a bulb cutting head configuration of the cutting device;

FIG. 20 is an end view of the cutting head of FIG. 19b having a rounded style entry tip configuration;

FIG. 21a is a top view of a cervical version of the cutting device;

FIG. 21b is a side view of the cutting device of FIG. 21a; and

FIG. 22 is a top view of a cutting device illustrating an alternate shaft configuration.

DETAILED DESCRIPTION

Figure 3:
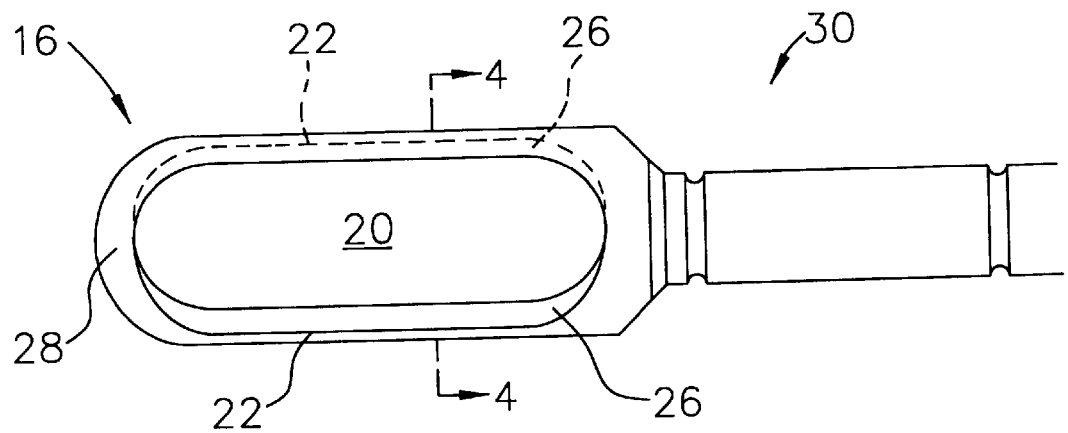
FIG. 3 is a partial detail view of the cutting device of FIG. 1 illustrating the cutting head, including the angled blade configuration and the entry tip.

Referring to FIGS. 1 and 2, the surgical cutting device 10 of the present invention is shown. The surgical cutting device comprises a mounting shaft 12, a main shaft 14 attached to the mounting shaft, and a cutting head 16 positioned at the opposite end of main shaft 14. The main shaft also includes engraved depth indicators 18 positioned on the main shaft adjacent to the cutting head. The cutting head, main shaft, and mounting shaft are an integral piece of hardened surgical steel, wherein the mounting shaft is connected to a rotary drill so that the cutting device can be rotated allowing the cutting head to operate.

Figure 4:
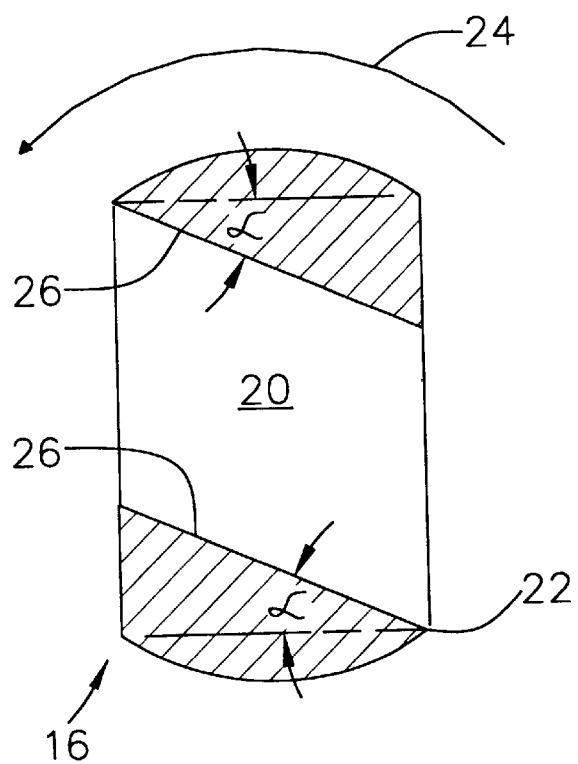
FIG. 4 is a cross-sectional view of the cutting head taken along line 4—4 of FIG. 3.

Referring to FIGS. 3 and 4, the components of the cutting head 16 are shown in greater detail. The cutting head includes a window 20 machined through the cutting head defining two cutting blades 22 on a leading edge of the cutting head as the cutting device is rotated in a counterclockwise direction 24. Window 20 is machined through the cutting head defining angled walls 26 through the depth of the cutting head. Walls 26 are at an angle α approximately 15–30° relative to a central bisecting plane "p" extending between the cutting blades. The cutting blades can be smooth as shown in FIG. 3 or serrated. Window 20 provides an area for removed tissue to accumulate and be further reduced in density, due to the rotation of the cutting blades. The removed material is essentially liquified and removed by aspiration. It is to be understood that for a cutting device rotatable in a clockwise direction, the configuration of the cutting blades and tapered walls would be a mirror image of that depicted in FIG. 4. The window 20 as shown in FIGS. 1–4 is elliptical or oval in shape, however, other shaped windows are contemplated as discussed subsequently herein.

Another important aspect of the cutting head is the entry tip configuration 28. FIGS. 5–7 illustrate an arrow style entry tip 30 for the cutting device 10. The arrow style entry tip has an elliptical perimeter 32 with a converging sloping surface 34 which converges in a rounded point 36. FIGS. 8–10 illustrate an alternative entry tip configuration being a bullet style entry tip 38. Bullet style entry tip includes a circular outer perimeter 40 having a sloping converting surface 42 terminating in a rounded point 44.

FIGS. 11–13 illustrate a second alternative entry tip configuration being an elliptical style entry tip 46. Elliptical style entry tip 46 includes an elliptical perimeter 48 with an arcuate rounded outer surface 50.

The cutting device of the present invention has dimensions that are practical for entry into the spinal intervertebral disc space for the various regions of the spine. The typical outside diameter or width of the cutting head will range from about 3 to about 13 millimeters. Widths of the cutting head can also range from about 5 to about 9 millimeters. The cutting head is balanced around the axis of the device so that the device will not wobble during rotation.

Figure 14:
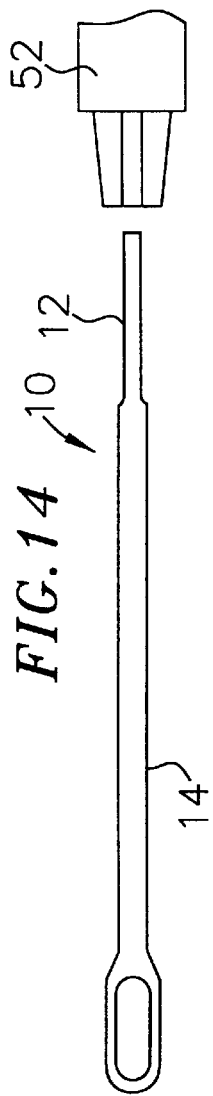
FIG. 14 is a top view of the cutting device of FIG. 1 illustrating the approximate length of the device for use in a non-cannulated open back surgical procedure.

As seen best in FIG. 14, the typical length of the cutting device 10 of the present invention for use in a non-cannulated fashion is from about 3 inches to about 6 inches. This length provides the necessary shaft length for insertion into a surgical drill and drill guard. The mounting shaft 12 of the cutting device has a reduced diameter from the main shaft 14 for insertion into the surgical drill collet 52.

Figure 15:
FIG. 15 is a top view of the cutting device of FIG. 1 illustrating the relational length of the device for use in a cannulated endoscopic surgical procedure.

FIG. 15 illustrates the typical length of the cutting device for use in a cannulated, endoscopic fashion and is from about 8 inches to about 12 inches. This length provides the necessary main shaft 14 length for insertion into the surgical drill and a standard surgical cannula (not shown) and provides the necessary extension of the entry tip 28 from the cannula for entry into the intervertebral disc. The outside diameter of the cannulated endoscopic device is that necessary to fit in close tolerance with the inside diameter of a standard surgical cannula.

The length of all embodiments of the cutting device of the present invention typically could increase in increments of ½ inch. The mounting shaft diameter 12 typically would be 0.092 inches or 0.125 inches based upon currently available surgical drill mounting collets 52.

Figure 17A:
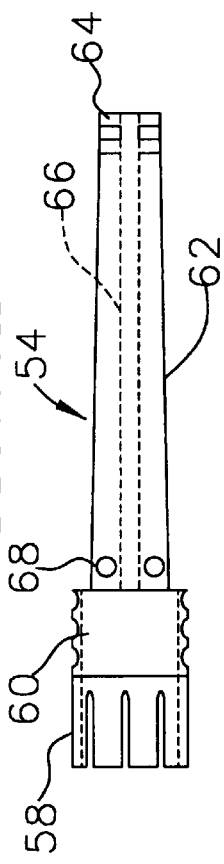
FIG. 17a is a side view of a drill guard for use in an open back surgical procedure.
Figure 17B:
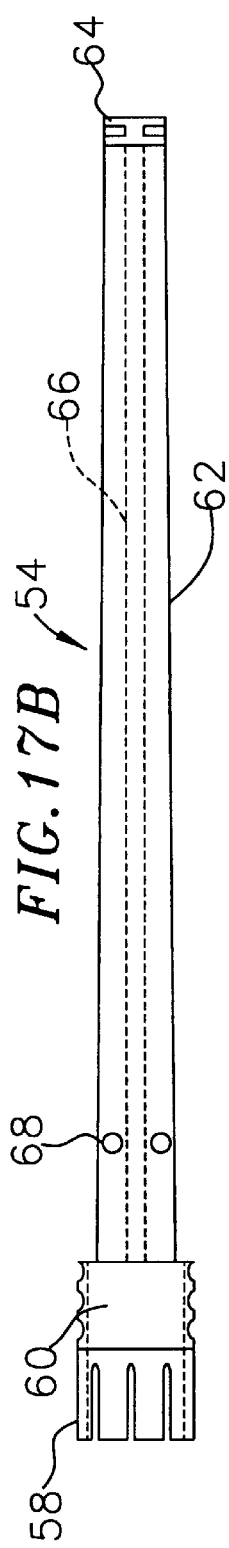
FIG. 17b is a side view of a drill guard for use in an endoscopic surgical procedure.

FIGS. 17a and 17b illustrate standard surgical drill guards, wherein FIG. 17a depicts an open back surgery drill guard 54 and FIG. 17b depicts an endoscopic surgery drill guard 56. The difference between drill guards 54 and 56 is the overall length of the guard. Guards 54 and 56 are made of surgical steel tubing that slides onto the collet 52 of the drill and is held in place by friction. More specifically, guards 54 and 56 include a friction sleeve 58 which slides over the drill collet 52. Drill guards 54 and 56 further include a finger pull 60 for insertion and removal of the drill guard and a guard body 62 extending from the finger pull 60. A stabilizer bushing 64 is positioned at the end of the guard body 62. A shaft opening 66 extends along the length of the guard for insertion of the cutting device. Vent holes 68 are typically located along the length of the guard body 72 at given intervals. Standard commercially available guards or custom made guards that are slightly longer and have a slightly larger internal diameter may be used with the cutting device of the present invention.

FIG. 18 illustrates a self-aspirating cutting device 70 which includes an aspiration channel 72 extending along the length of the mounting shaft 74, main shaft 76 and terminating at window 80 in cutting head 78. The aspiration channel terminates in openings 82 and 84, in the window of the cutting head and in the mounting shaft, respectively. The aspiration channel of the cutting device is for aspiration of the removed material.

Figure 16:
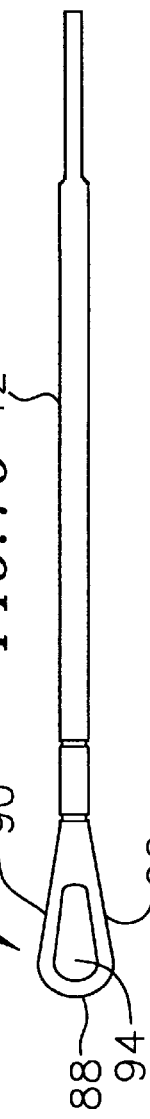
FIG. 16 is a top view of a alternative embodiment cutting device having a rounded style entry tip configuration.

The geometrical shape of the cutting head can also be varied. The cutting head 16 of the cutting device embodiments referenced herein illustrate a generally elliptical cutting head. Alternative cutting head geometries can be seen in FIGS. 16, 19a and 19b. FIG. 16 illustrates a tear drop cutting head configuration 86 having a rounded entry tip 88 and includes converging walls 90 extending from entry tip 88 to main shaft 92. In the tear drop configuration the cutting head includes a tear drop shaped window 94. FIG. 19a illustrates a round cutting head configuration 96. In this configuration the cutting head includes a rounded outer wall 98 extending from the main shaft 100. The round cutting head also includes a circular window 102. FIG. 19b illustrates a bulb cutting head configuration 104 having a rounded entry tip 106 and generally parallel side walls 108. Converging back walls 110 extend from the main shaft 112 to the parallel side walls 108. The bulb cutting head configuration includes a generally elliptical or oval window 114. In each of the tear drop cutting head configuration, round head configuration, and bulb head configuration, the entry tips have a rounded configuration as shown in FIG. 20. The rounded entry tip includes an oval perimeter 116 and a rounded outer surface 118.

Although the present invention has been described and is illustrated with respect to various embodiments thereof, it is to be understood that it is not to be so limited, since changes and modifications may be made therein which are within the full intended scope of the invention as hereinafter claimed. For example, FIGS. 21a and 21b illustrate a cervical cutting device 120 wherein the mounting shaft 122 and main shaft 124 are of equal diameter. The cervical cutting tool preferably would have an overall length of 2.75 inches and a cutting head diameter of 0.125 inches. As seen in FIG. 21b, the height of the cutting head 126 is equal to the diameter of the main shaft.

FIG. 22 illustrates yet another alternative cutting device 128 having a tapered main shaft 130 without fillets at the juncture between the main shaft and the mounting shaft 132. Cutting device 128, by having a tapered main shaft, provides a design having improved strength and rotational stability for longer shaft lengths.

What is claimed is:

1. A cutting device for removing tissue matter from a surgical site during a surgical procedure, which comprises:

means for emulsifying the tissue matter during a surgical procedure;

the emulsifying means including a cutting head having an entry tip dimensioned to facilitate entry of the cutting head within the tissue matter and two cutting blades, and defining an axis about which the cutting head rotates, each cutting blade positioned with respect to the axis to define a window extending through the cutting head, each cutting blade defining a leading cutting edge adapted to cut the tissue matter upon rotation of the cutting head in one direction of rotation, the cutting blades dimensioned and configured to generally direct tissue portions cut by the cutting edges to the window of the cutting head whereby the cut tissue portions are at least partially emulsified upon continued rotation of the cutting head, each cutting blade defining an interior wall portion extending continuously at a fixed angle from the leading cutting edge substantially through the cutting head; and means for rotatably supporting the emulsifying means during the surgical procedure.

2. The cutting device of claim 1 wherein the window in the emulsifying means defines two walls extending at an angle from each cutting blade.

3. The cutting device of claim 2 wherein the walls extend at an angle from about 15° to about 30° from a horizontal plane extending perpendicular to an opening of the window.

4. The cutting device of claim 1 wherein the emulsifying means is a generally elliptically shaped cutting head.

5. The cutting device of claim 4 wherein the support means comprises a main shaft and a mounting shaft.

6. The cutting device of claim 5 wherein the main shaft, mounting shaft and cutting head are formed from a single piece of hardened surgical steel.

7. The cutting device of claim 6 wherein the cutting head, main shaft and mounting shaft include an aspiration channel for the aspiration of removed matter.

8. The cutting device of claim 5 wherein the main shaft includes depth indicators.

9. The cutting device of claim 1 wherein the entry tip is generally elliptically shaped.

10. The cutting device of claim 1 wherein the entry tip is generally bullet shaped.

11. The cutting device of claim 1 wherein the entry tip is generally arrow shaped.

12. The cutting device of claim 1 wherein the support means is a tapered shaft.

13. The cutting device of claim 1 wherein the emulsifying means is a generally round shaped cutting head.

14. The cutting device of claim 1 wherein the emulsifying means is a generally tear drop shaped cutting head.

15. The cutting device of claim 1 wherein the emulsifying means is a generally bulb shaped cutting head.

16. The cutting device of claim 1 wherein at least some of the matter to be removed is soft tissue.

17. The cutting device of claim 1 wherein at least some of the matter to be removed is bone mass.

18. The cutting device of claim 1 wherein said emulsifying means has a center of gravity located at a central axis extending along a length thereof.

19. The cutting device of claim 1 wherein the support means comprises a main shaft and a mounting shaft, said mounting shaft having a diameter adapted for insertion into a surgical drill.

20. The cutting device of claim 1 further comprising a guard for sliding onto a collet of a drill, said guard having an opening extending along a length thereof for insertion of the supporting means.

21. A surgical cutting device for emulsifying matter from a surgical site comprising:

a cutting head having an entry tip adapted to facilitate entry of the cutting head into tissue matter and two substantially rigid, autonomous cutting blades, each cutting blade located on opposed edges of a window extending through an interior portion of the cutting head such that each cutting blade forms a leading edge adapted to cut the tissue matter in the same direction of rotation, each cutting blade defining an interior wall portion extending continuously at a fixed angle from the leading edge substantially through the cutting head; and a shaft connected to the cutting head for mounting the cutting head to a rotary surgical drill.

22. The cutting device of claim 21 wherein the window in the cutting head includes two walls extending at an angle from each cutting blade.

23. The cutting device of claim 21 wherein an aspiration channel extends from the cutting head through the main shaft for aspirating emulsified matter.

24. The cutting device of claim 21 wherein at least some of the matter to be emulsified is soft tissue.

25. The cutting device of claim 21 wherein at least some of the matter to be emulsified is bone mass.

26. A surgical cutting device comprising:

a shaft connectable to a rotary surgical drill and defining a longitudinal axis;

a cutting head mounted to the shaft for cutting and reducing tissue matter;

the cutting head including an entry tip and two cutting blades, each cutting blade arranged about the longitudinal axis to define a window extending through the cutting head, the cutting blades having interior wall portions disposed adjacent the window, each interior wall portion arranged at a predetermined angle with respect to the longitudinal axis and extending continuously substantially through the cutting head at the predetermined angle to terminate in a leading cutting edge, the leading cutting edges adapted to cut tissue matter upon rotation of the cutting head in one direction of rotation.

27. The cutting device of claim 26 further having an aspiration channel extending from the cutting head through the shaft for aspirating reduced matter.

28. A surgical cutting device for emulsifying matter from a surgical site, comprising:

a main shaft defining a longitudinal axis;

a mounting shaft positioned at one end of the main shaft, the mounting shaft having a diameter adapted for insertion into a surgical drill; and a cutting head positioned at another end of the main shaft opposite the mounting shaft, the cutting head having an entry tip and first and second cutting elements arranged about the longitudinal axis to define a window extending through an interior portion of the cutting head, each cutting element defining a leading cutting edge adapted to cut in the same direction of rotation and being located on an opposed edge of the window, and having an angled wall extending continuously from the leading cutting edge substantially through the cutting head at a predetermined angle, the angled wall dimensioned to facilitate directing of tissue portions cut by the cutting elements into the window whereby the cut tissue portions are at least partially emulsified upon continued rotation of the cutting head.

29. The cutting device of claim 21 wherein each cutting blade is dimensioned to extend at a fixed angle.

30. The cutting device of claim 29 wherein the leading edges of the cutting blades are adapted to cut tissue matter encountered through 360° in the same direction of rotation.

31. The cutting device of claim 28 wherein the angled wall of each cutting element is dimensioned to extend substantially through the cutting head.

32. A cutting device for emulsifying a variety of different types of matter from a surgical site during a surgical procedure comprising:

means for emulsifying the variety of different types of matter during the surgical procedure;

said emulsifying means including an entry tip adapted to provide an entry of the cutting head into the variety of different types of matter to be cut by the cutting head and two hardened, autonomous, stand alone cutting blades, the cutting blades each having an interior wall arranged at a fixed angle relative to a central bisecting plane extending between the cutting blades and extending continuously substantially through the cutting head at the fixed angle, the interior walls defining a window therebetween such that each cutting blade defines a leading edge adapted to cut through the variety of different types of matter it encounters through 360° in the same direction of rotation; and means for rotatably supporting the emulsifying means during the surgical procedure.

* * * * *